(12) United States Patent
Kathirgamanathan et al.

(10) Patent No.: US 7,642,548 B2
(45) Date of Patent: Jan. 5, 2010

(54) ELECTROLUMINESCENT MATERIALS AND DEVICES

(75) Inventors: Poopathy Kathirgamanathan, North Harrow (GB); Subramaniam Ganeshamurugan, London (GB)

(73) Assignee: Merck Patent GmbH, Darmstadt (DE)

( * ) Notice: Subject to any disclaimer, the term of this patent is extended or adjusted under 35 U.S.C. 154(b) by 458 days.

(21) Appl. No.: 11/661,074

(22) PCT Filed: Aug. 5, 2005

(86) PCT No.: PCT/GB2005/050128
§ 371 (c)(1),
(2), (4) Date: Mar. 23, 2007

(87) PCT Pub. No.: WO2006/024878
PCT Pub. Date: Mar. 9, 2006

(65) Prior Publication Data
US 2007/0272920 A1    Nov. 29, 2007

(30) Foreign Application Priority Data
Aug. 31, 2004   (GB)  .................. 0419269.6

(51) Int. Cl.
*H01L 51/54* (2006.01)
*C07D 339/08* (2006.01)
*C09K 11/06* (2006.01)

(52) U.S. Cl. ................. 257/40; 257/103; 257/E51.044; 428/917; 549/20; 252/301.16

(58) Field of Classification Search .................. 252/301.16–301.18; 257/40, 103, E51.044; 313/504; 428/690, 917; 549/20
See application file for complete search history.

(56) References Cited

U.S. PATENT DOCUMENTS

2006/0127696 A1   6/2006  Stossel et al.

FOREIGN PATENT DOCUMENTS

EP        1 239 526         9/2002

OTHER PUBLICATIONS

Lamansky, S., et al. "Highly Phosphorescent Bis-Cyclometalated Iridium Complexes: Synthesis, Photophysical Characterization, and Use in Organic Light Emitting Diodes." J. Am. Chem. Soc., vol. 123 (2001): pp. 4304-4312.*

* cited by examiner

*Primary Examiner*—Douglas M Menz
*Assistant Examiner*—Matthew W Such
(74) *Attorney, Agent, or Firm*—David Silverstein; Andover-IP-Law

(57) ABSTRACT

Novel ruthenium, rhodium, palladium, osmium, iridium or platinum complexes of thianthrene ligands are electroluminescent compounds. According to the invention there is provided complexes of Formula (I).

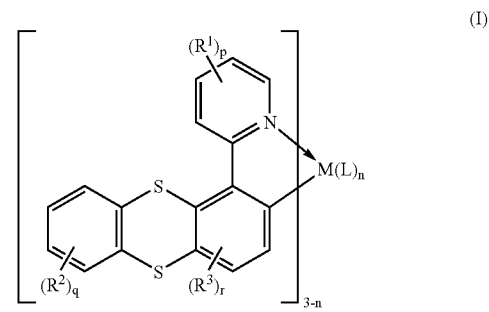

20 Claims, 7 Drawing Sheets

Alq

Bebq

BAlq1

ZnPBO

ZnPBT

DTVbi

Alq

Bebq

BAlq1

ZnPBO

ZnPBT

DTVb1 or

α-NPB

TPD mTADATA

ELECTROLUMINESCENT MATERIALS AND DEVICES

CROSS-REFERENCE TO RELATED APPLICATIONS

Figure 1:
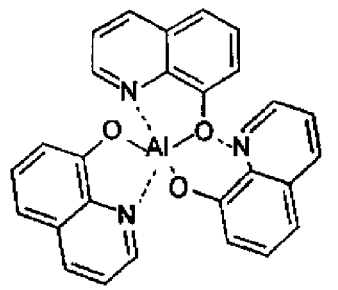
Figure 1:
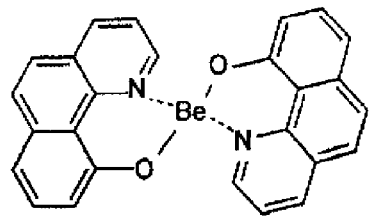
Figure 1:
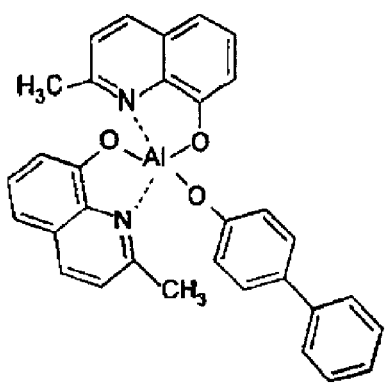
Figure 1:
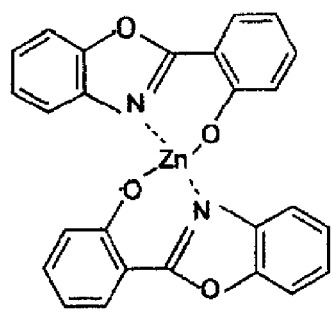
Figure 1:
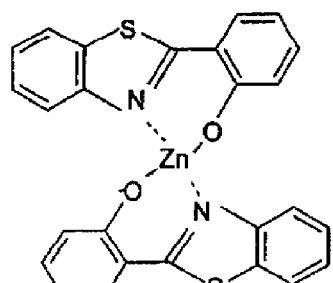
Figure 1:
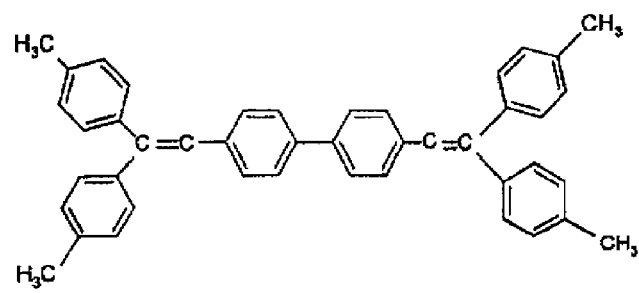

This application claims benefit of the filing date of international application PCT/GB05/50128 filed Aug. 5, 2005, which claims the benefit of the filing date of United Kingdom application no. 0419269.6 filed Aug. 31, 2004.

The present invention relates to electroluminescent materials and to electroluminescent devices.

Materials that emit light when an electric current is passed through them are well known and used in a wide range of display applications. Devices which are based on inorganic semiconductor systems are widely used. However these suffer from the disadvantages of high energy consumption, high cost of manufacture, low quantum efficiency and the inability to make flat panel displays. Organic polymers have been proposed as useful in electroluminescent devices, but it is not possible to obtain pure colours; they are expensive to make and have a relatively low efficiency. Another electroluminescent compound which has been proposed is aluminium quinolate, but it requires dopants to be used to obtain a range of colours and has a relatively low efficiency.

Patent application WO98/58037 describes a range of transition metal and lanthamide complexes which can be used in electroluminescent devices which have improved properties and give better results. Patent Applications PCT/GB98/01773, PCT/GB99/03619, PCT/GB99/04030, PCT/GB99/04024, PCT/GB99/04028 and PCT/GB00/00268 describe electroluminescent complexes, structures and devices using rare earth chelates. U.S. Pat. No. 5,128,587 discloses an electroluminescent device which consists of an organometallic complex of rare earth elements of the lanthamide series sandwiched between a transparent electrode of high work function and a second electrode of low work function, with a hole conducting layer interposed between the electroluminescent layer and the transparent high work function electrode, and an electron conducting layer interposed between the electroluminescent layer and the electron injecting low work function anode. The hole conducting layer and the electron conducting layer are required to improve the working and the efficiency of the device. The hole transporting layer serves to transport holes and to block the electrons, thus preventing electrons from moving into the electrode without recombining with holes. The recombination of carriers therefore mainly takes place in the emitter layer.

We have now discovered further electroluminescent organometallic complexes.

According to the invention there is provided complexes of formula I:

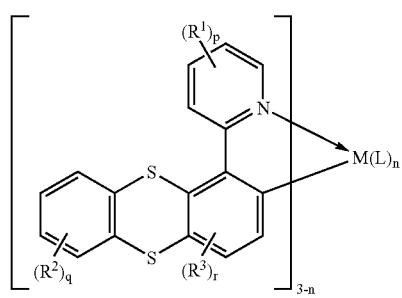

wherein
L is

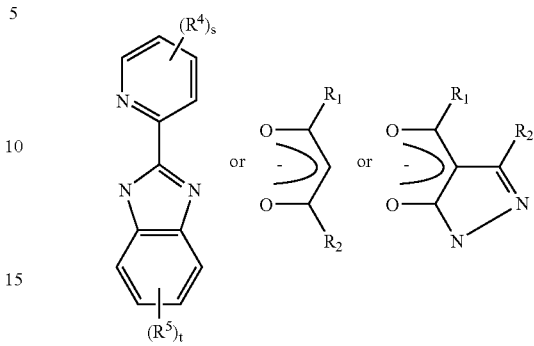

M is ruthenium, rhodium, palladium, osmium, iridium or platinum;

n is 1 or 2;

$R_1$, $R_4$ and $R_5$ can be the same or different and are selected from
  substituted and unsubstituted hydrocarbyl groups
  substituted and unsubstituted monocyclic and polycyclic heterocyclic groups;
  substituted and unsubstituted hydrocarbyloxy or carboxy groups;
  fluorocarbyl groups;
  halogen;
  nitrile;
  amino;
  alkylamino;
  dialkylamino,
  arylamino,
  diarylamino
  and thiophenyl;

p, s and t independently are 0, 1, 2 or 3;

subject to the proviso that where any of p, s and t is 2 or 3 only one of them can be other than saturated hydrocarbyl or halogen;

$R_2$ and $R_3$ can be the same or different and are selected from substituted and unsubstituted hydrocarbyl groups halogen;

q and r independently are 0, 1 or 2.

Preferred compounds of the above class are those in which M is iridium. The preferred value for n is 1.

In those compounds which are ring-substituted, $R_1$, $R_4$ and $R_5$ may be a substituted or unsubstituted aliphatic or cycloaliphatic group which may typically be $C_1$-$C_{12}$ and in the case of a cycloaliphatic group are preferably based on cyclopentyl or cyclohexyl. Where $R_1$, $R_4$ and $R_5$ are alkyl they are preferably $C_1$-$C_4$ especially methyl or ethyl. $R_1$, $R_4$ and $R_5$ may also be alkyl or alkoxy in which the alkyl group is preferably $C_1$-$C_{12}$, more preferably $C_1$-$C_4$. Thus preferred values for at least one of $R_1$, $R_4$ and $R_5$ are methyl, ethyl, n-propyl, i-propyl. s-butyl, t-butyl, cyclohexyl, methoxy or ethoxy. In further possibilities, at least one of $R_1$, $R_4$ and $R_5$ is a substituted or unsubstituted monocyclic or polycyclic aromatic, aryloxy or heterocyclic structure. For example, at least one of $R_1$, $R_4$ and $R_5$ may be phenyl, tolyl, fluorophenyl, biphenyl, naphthyl, fluorenyl, anthracenyl, phenanthrenyl or carbazolyl. Other possibilities for at least one of $R_1$, $R_4$ and $R_5$ are fluoro, chloro, methylamino, dimethylamino, benzylamino or dibenzylamino.

In those compounds which are ring-substituted, $R_2$ and $R_3$ may be a substituted or unsubstituted aliphatic group. Where $R_2$ and $R_3$ are alkyl they are preferably $C_1$-$C_4$ especially methyl or ethyl. Other possibilities for at least one of $R_2$ and $R_3$ are chloro or bromo.

A particular compound of formula (I) above is that in which M is Ir, n is 1 and p, q, r, s and t are 0.

According to a further aspect of the invention, there is also provided a process for manufacturing a compound of formula (I) as defined above.

Thianthrenes and substituted derivatives thereof may be prepared by treating a benzene compound with sulfur monochloride in the presence of aluminium trichloride catalyst according to the procedure described in U.S. Pat. No. 4,139,516 and U.S. Pat. No. 4,091,031, the required halogenated material being separated from other reaction products in manner known per se e.g. HPLC:

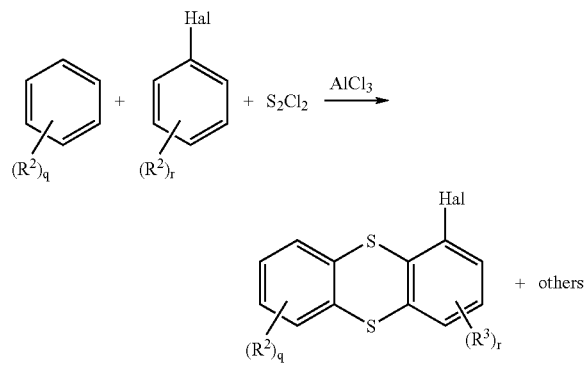

The product may then be converted to a thianthren-1-yl-boronic acid by treatment with a magnesium halide and a trialkyl borate in manner known per se. Synthesis of the desired 2-(thianthren-1-yl)pyridine may be achieved by a Suzuki coupling of a 2-bromopyridine with the thianthren-1-yl-boronic acid using a palladium (0) catalyst, for example tetrakis(triphenylphosphine) palladium e.g. according to the scheme shown below:

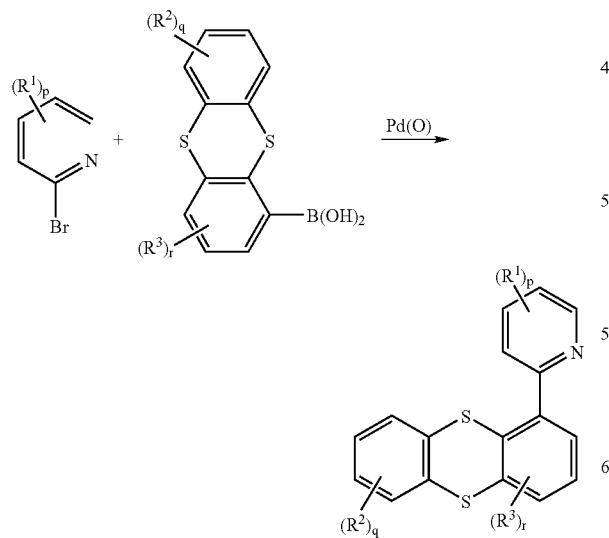

Heating 2-(thianthren-1-yl)pyridine or a substituted derivative thereof with iridium trichloride gives e.g. the following complex:

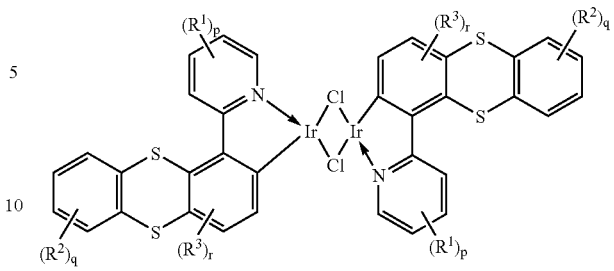

Further treatment of the above complex with a strong base and addition of (2-pyridyl)benzimidazole or a substituted derivative thereof produces the compound of formula (I), the substituents having the same meanings as for formula (I).

In the first step, instead of benzene there may be used, for example, toluene, o-chlorotoluene, m-chlorotoluene, p-chlorotoluene, o-xylene or m-xylene.

In the second step instead of 2-bromopyridine there may be used, for example, 2-chloro-5-iodopyridine, 2-bromo-5-iodopyridine or 2-amino-5-iodopyridine.

The invention also provides an electroluminescent device which comprises (i) a first electrode, (ii) a layer of an electroluminescent material of formula (I) above and (iii) a second electrode.

The thickness of the layer of the electroluminescent material is preferably from 10-250 nm, more preferably 20-75 nm.

The first electrode can function as the anode and the second electrode can function as the cathode and preferably there is a layer of a hole transporting material between the anode and the layer of the electroluminescent compound.

The hole transporting material can be any of the hole transporting materials used in electroluminescent devices.

The hole transporting material can be an amine complex such as α-NBP, poly (vinylcarbazole), N,N'-diphenyl-N,N'-bis(3-methylphenyl)-1,1'-biphenyl-4,4'-diamine (TPD), an unsubstituted or substituted polymer of an amino substituted aromatic compound, a polyaniline, substituted polyanilines, polythiophenes, substituted polythiophenes, unsubstituted and substituted polysilanes etc. Examples of polyanilines are polymers of:

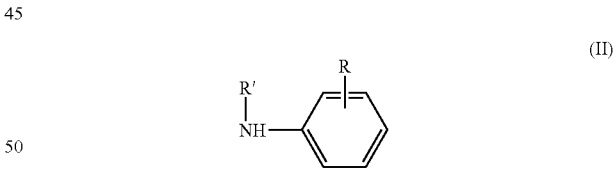

where R is in the ortho- or meta-position and is hydrogen, C1-18 alky, C1-6 alkoxy, amino, chloro, bromo, hydroxy or the group:

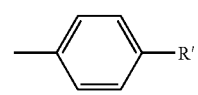

where R is alkyl or aryl and R' is hydrogen, C1-6 alkyl or aryl with at least one other monomer of formula II above.

Alternatively the hole transporting material can be a polyaniline. Polyanilines which can be used in the present invention have the general formula:

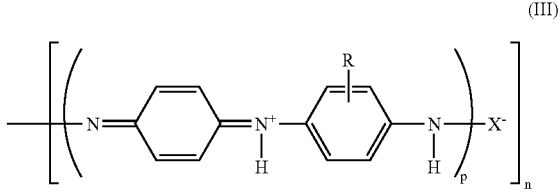

(III)

where p is from 1 to 10 and n is from 1 to 20, R is as defined above and X is an anion, preferably selected from Cl, Br, SO$_4$, BF$_4$, PF$_6$, H$_2$PO$_3$, H$_2$PO$_4$, arylsulphonate, arenedicarboxylate, polystyrenesulphonate, polyacrylate alkylsulphonate, vinylsulphonate, vinylbenzene sulphonate, cellulose sulphonate, camphor sulphonate, cellulose sulphate or a perfluorinated polyanion.

Examples of arylsulphonates are p-toluenesulphonate, benzenesulphonate, 9,10-anthraquinone-sulphonate and anthracenesulphonate. An example of an arenedicarboxylate is phthalate and an example of arenecarboxylate is benzoate.

We have found that protonated polymers of the unsubstituted or substituted polymer of an amino substituted aromatic compound such as a polyaniline are difficult to evaporate or cannot be evaporated. However we have surprisingly found that if the unsubstituted or substituted polymer of an amino substituted aromatic compound is deprotonated, then it can be easily evaporated, i.e. the polymer is evaporable.

Preferably evaporable deprotonated polymers of unsubstituted or substituted polymers of an amino substituted aromatic compound are used. The deprotonated unsubstituted or substituted polymer of an amino substituted aromatic compound can be formed by deprotonating the polymer by treatment with an alkali such as ammonium hydroxide or an alkali metal hydroxide such as sodium hydroxide or potassium hydroxide.

The degree of protonation can be controlled by forming a protonated polyaniline and deprotonating. Methods of preparing polyanilines are described in the article by A. G. Mac-Diamid and A. F. Epstein, Faraday Discussions, Chem. Soc. 88 P 319, 1989.

The conductivity of the polyaniline is dependent on the degree of protonation with the maximum conductivity being when the degree of protonation is between 40 and 60%, for example about 50%.

Preferably the polymer is substantially fully deprotonated.

A polyaniline can be formed of octamer units. i.e. p is four, e.g.

Other polymers of an amino substituted aromatic compound which can be used include substituted or unsubstituted polyaminonapthalenes, polyaminoanthracenes, polyaminophenanthrenes, etc. and polymers of any other condensed polyaromatic compound. Polyaminoanthracenes and methods of making them are disclosed in U.S. Pat. No. 6,153,726. The aromatic rings can be unsubstituted or substituted, e.g. by a group R as defined above.

Other hole transporting materials are conjugated polymers and the conjugated polymers which can be used can be any of the conjugated polymers disclosed or referred to in U.S. Pat. No. 5,807,627, WO90/13148 and WO92/03490.

The preferred conjugated polymers are poly (p-phenylenevinylene) (PPV) and copolymers including PPV. Other preferred polymers are poly(2,5 dialkoxyphenylene vinylene) such as poly[2-methoxy-5-(2-methoxypentyloxy-1,4-phenylene vinylene)], poly[(2-methoxypentyloxy)-1,4-phenylenevinylene], poly[(2-methoxy-5-(2-dodecyloxy-1,4-phenylenevinylene)] and other poly(2,5 dialkoxyphenylenevinylenes) with at least one of the alkoxy groups being a long chain solubilising alkoxy group, polyfluorenes and oligofluorenes, polyphenylenes and oligophenylenes, polyanthracenes and oligoanthracenes, polythiophenes and oligothiophenes.

In PPV the phenylene ring may optionally carry one or more substituents, e.g. each independently selected from alkyl, preferably methyl, or alkoxy, preferably methoxy or ethoxy.

In polyfluorene, the fluorene ring may optionally carry one or more substituents e.g. each independently selected from alkyl, preferably methyl, alkoxy, preferably methoxy or ethoxy.

Any poly(arylenevinylene) including substituted derivatives thereof can be used and the phenylene ring in poly(p-phenylenevinylene) may be replaced by a fused ring system such as anthracene or naphthalene ring and the number of vinylene groups in each poly(phenylenevinylene) moiety can be increased, e.g. up to 7 or higher.

The conjugated polymers can be made by the methods disclosed in U.S. Pat. No. 5,807,627, WO90/13148 and WO92/03490.

The thickness of the hole transporting layer is preferably 20 nm to 200 nm.

The polymers of an amino substituted aromatic compound such as polyanilines referred to above can also be used as buffer layers with or in conjunction with other hole transporting materials e.g. between the anode and the hole transporting layer. Other buffer layers can be formed of phthalocyanines such as copper phthalocyanine.

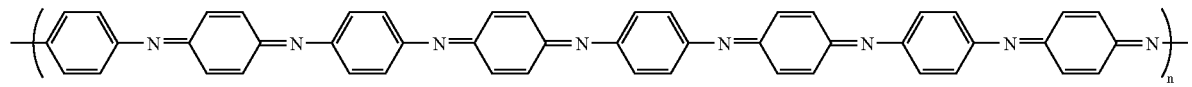

The polyanilines can have conductivities of the order of 1×10$^{-1}$ Siemen cm$^{-1}$ or higher.

The aromatic rings can be unsubstituted or substituted, e.g. by a C1 to 20 alkyl group such as ethyl.

The polyaniline can be a copolymer of aniline and preferred copolymers are the copolymers of aniline with o-anisidine, m-sulphanilic acid or o-aminophenol, or o-toluidine with o-aminophenol, o-ethylaniline, o-phenylene diamine or with amino anthracenes.

The structural formulae of some other hole transporting materials are shown in FIGS. 3, 4, 5, 6 and 7 of the drawings, where R, R$_1$, R$_2$, R$_3$ and R$_4$ can be the same or different and are selected from hydrogen, substituted and unsubstituted hydrocarbyl groups such as substituted and unsubstituted aliphatic groups, substituted and unsubstituted aromatic, heterocyclic and polycyclic ring structures, fluorocarbon groups such as trifluoromethyl, halogens such as fluorine or thiophenyl groups; R, R$_1$, R$_2$, R$_3$ and R$_4$ can also form substituted and unsubstituted fused aromatic, heterocyclic and polycyclic ring structures and can be copolymerisable with a monomer, e.g. styrene. X is Se, S or O, Y can be hydrogen, substituted or unsubstituted hydrocarboxyl groups, such as substituted and unsubstituted aromatic, heterocyclic and polycyclic ring structures, fluorocarbon groups such as trifluoromethyl, halogens such as fluorine, thiophenyl or nitrile groups.

Examples of R and/or $R_1$ and/or $R_2$ and/or $R_3$ and/or $R_4$ include aliphatic, aromatic and heterocyclic groups, alkoxy, aryloxy and carboxy groups, substituted and unsubstituted phenyl, fluorophenyl, biphenyl, naphthyl, fluorenyl, anthracenyl and phenanthrenyl groups, alkyl groups such as t-butyl, and heterocyclic groups such as carbazole.

Figure 2:
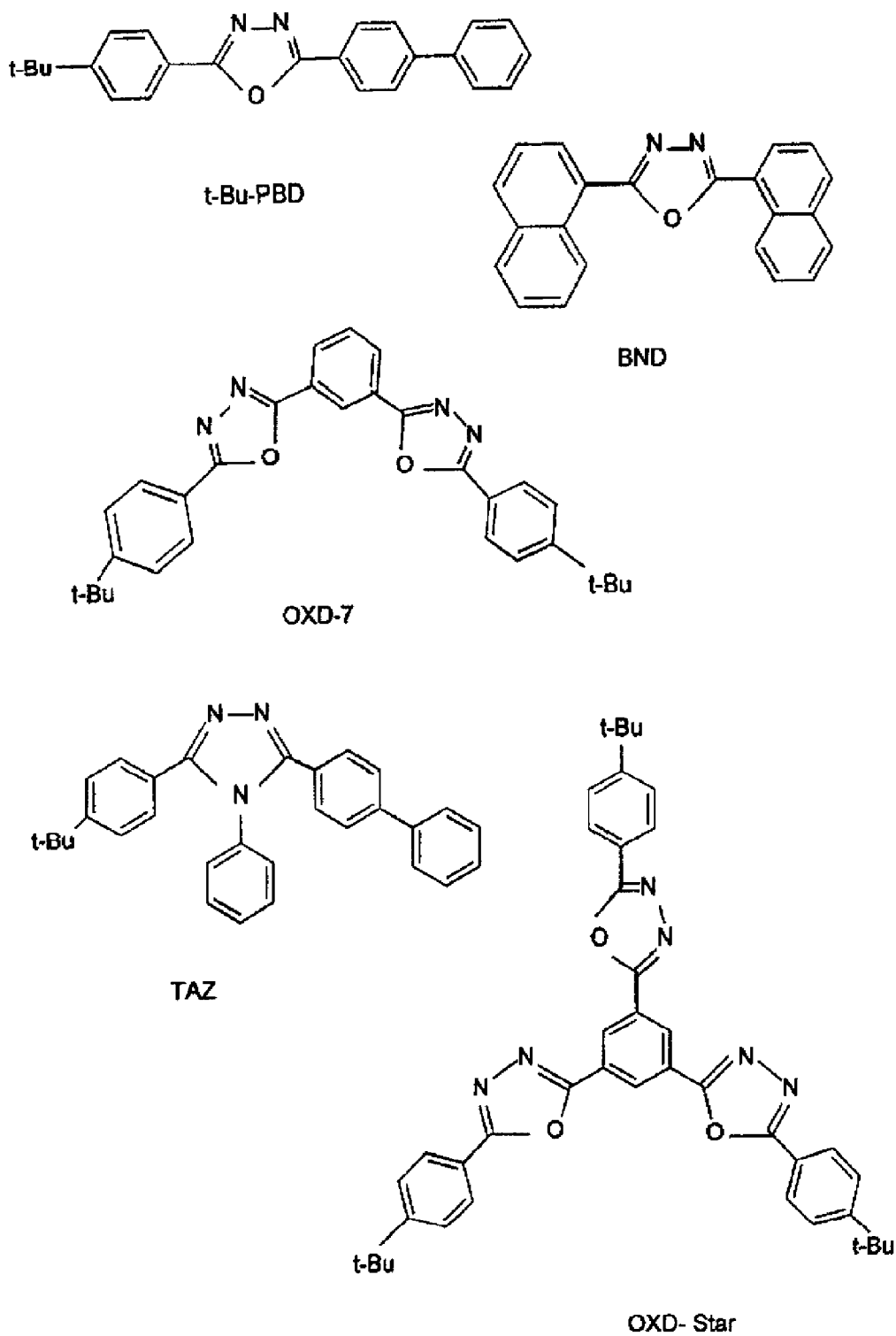
Figure 3:
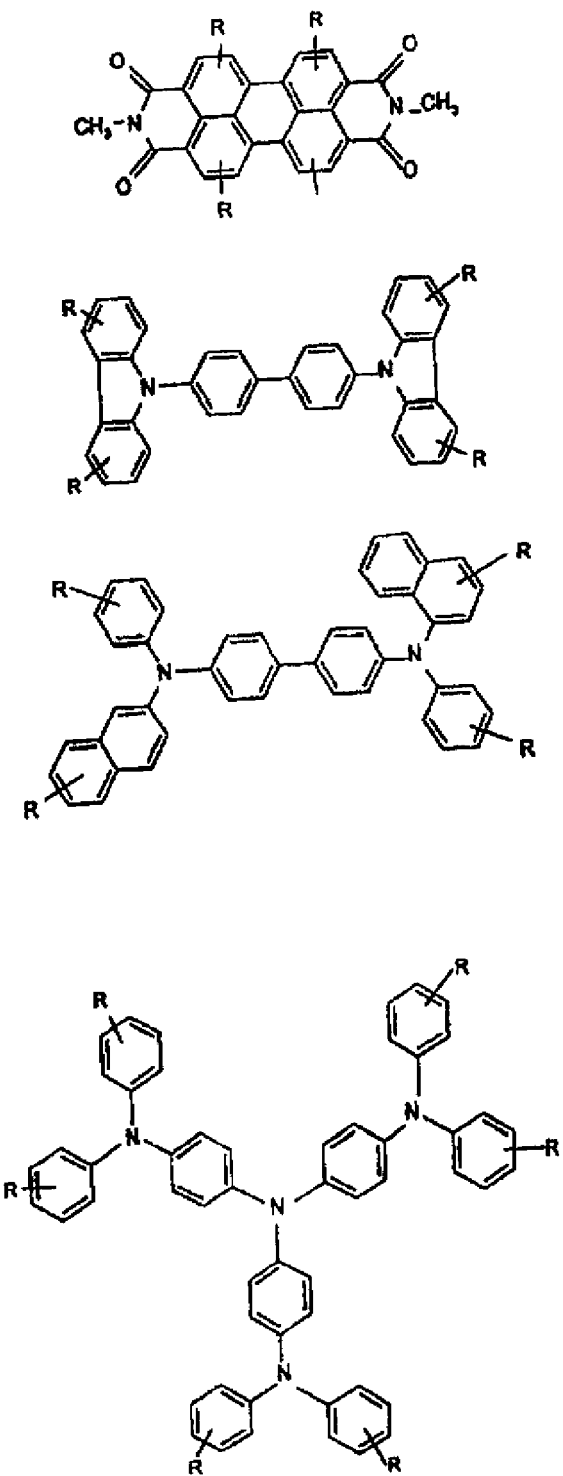
Figure 4:
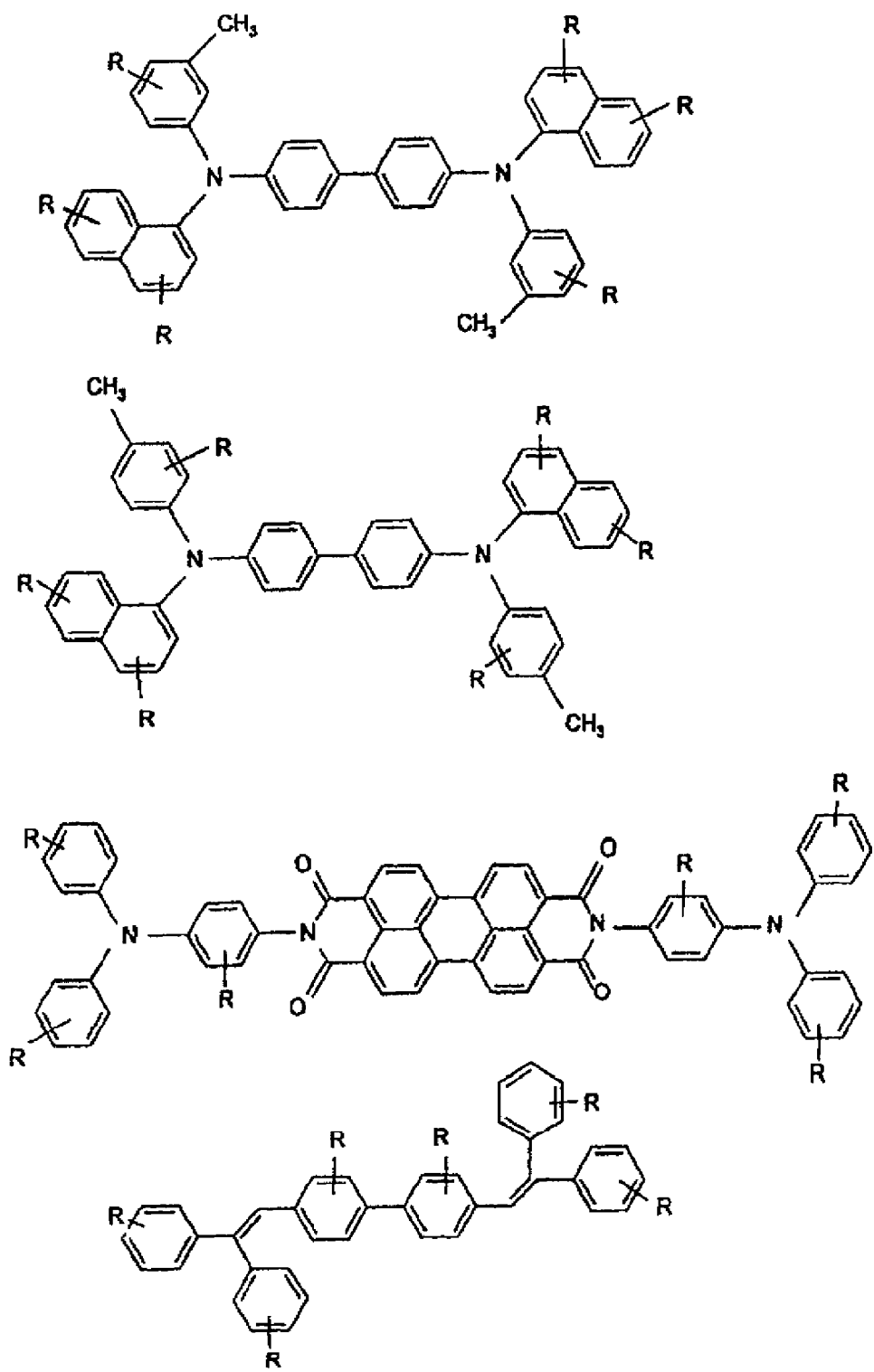
Figure 5:
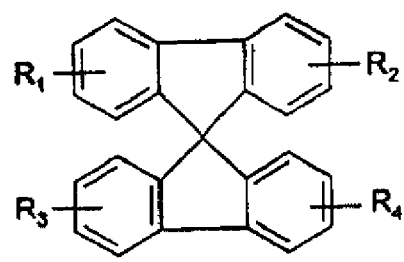
Figure 5:
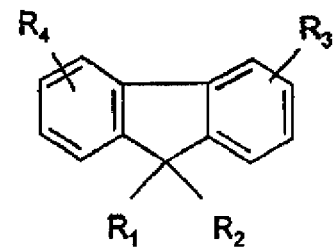
Figure 5:
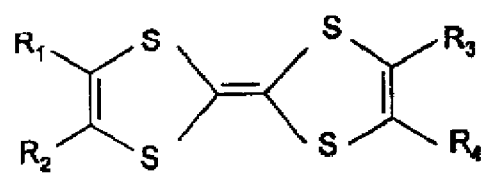
Figure 5:
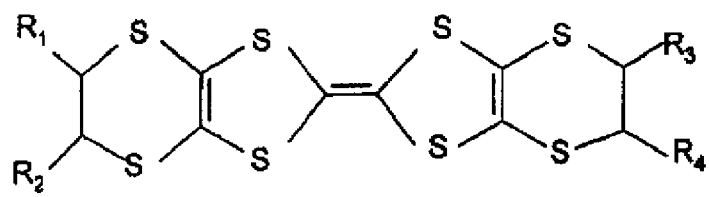
Figure 5:
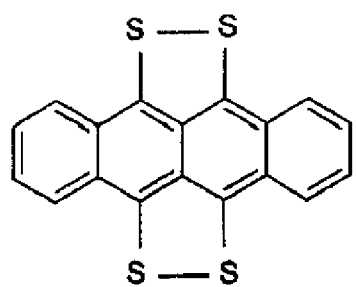
Figure 6:
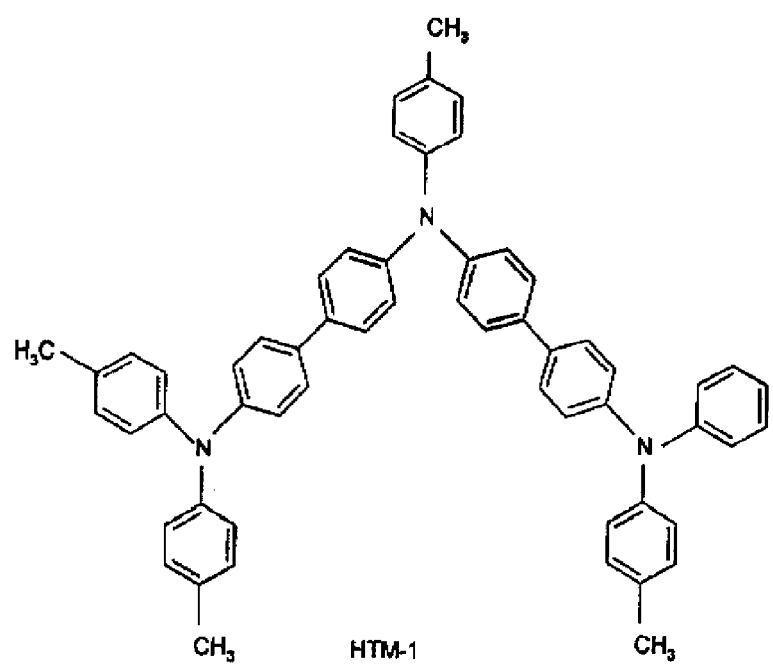
Figure 6:
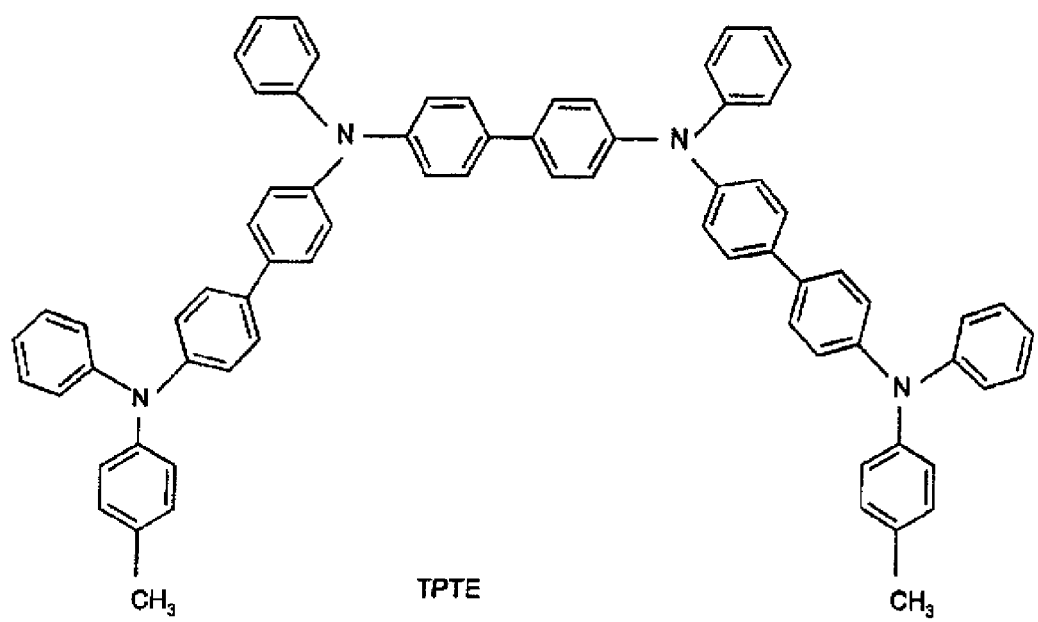
Figure 7:
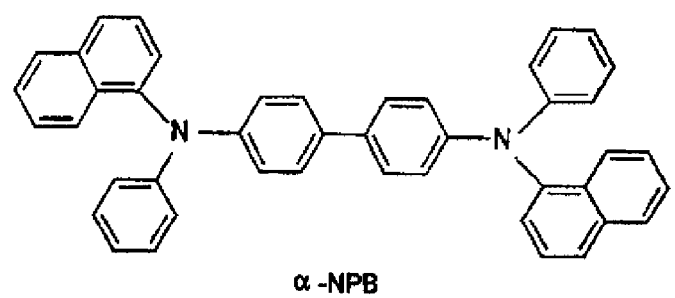
Figure 7:
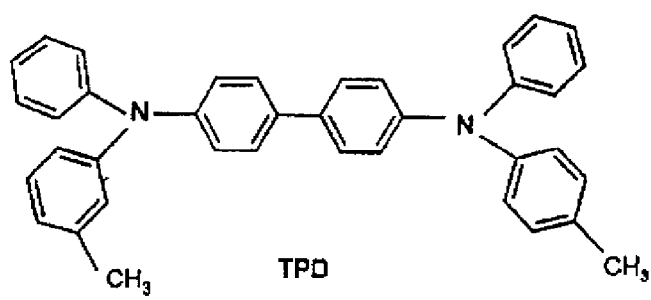
Figure 7:
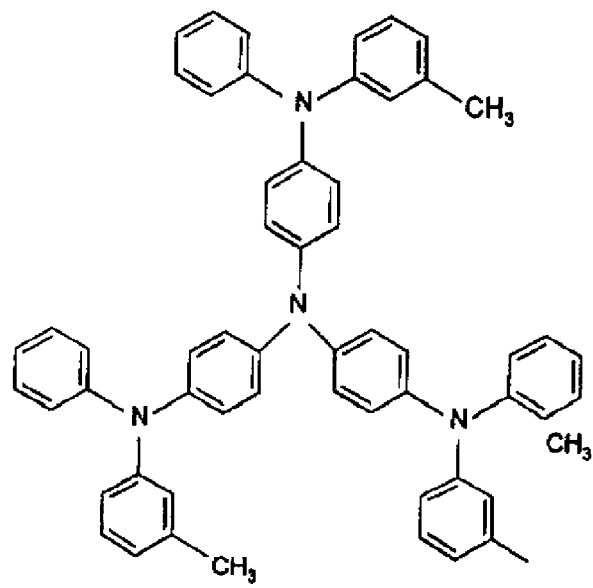

Optionally there is a layer of an electron injecting material between the anode and the electroluminescent material layer. The electron injecting material is a material which will transport electrons when an electric current is passed through. Electron injecting materials include a metal complex such as a metal quinolate, e.g. an aluminium quinolate, lithium quinolate, zirconium quinolate ($Zrq_4$), a cyanoanthracene such as 9,10-dicyanoanthracene, cyano substituted aromatic compounds, tetracyanoquinodimethane, a polystyrene sulphonate or a compound with the structural formulae shown in FIG. 1 or 2 of the drawings or $Mx(DBM)_n$ where Mx is a metal and DBM is dibenzoyl methane and n is the valency of Mx e.g. Mx is aluminium or chromium. A Schiff base can also be used in place of the DBM moiety.

Instead of being a separate layer the electron injecting material can be mixed with the electroluminescent material and co-deposited with it.

Optionally the hole transporting material can be mixed with the electroluminescent material and co-deposited with it and the electron injecting materials and the electroluminescent materials can be mixed. The hole transporting materials, the electroluminescent materials and the electron injecting materials can be mixed together to form one layer, which simplifies the construction.

The first electrode is preferably a transparent substrate such as a conductive glass or plastic material which acts as the anode; preferred substrates are conductive glasses such as indium tin oxide coated glass, but any glass which is conductive or has a conductive layer such as a metal or conductive polymer can be used. Conductive polymers and conductive polymer coated glass or plastics materials can also be used as the substrate.

The cathode is preferably a low work function metal, e.g. aluminium, barium, calcium, lithium, rare earth metals, transition metals, magnesium and alloys thereof such as silver/magnesium alloys, rare earth metal alloys etc; aluminium is a preferred metal. A metal fluoride such as an alkali metal e.g. lithium fluoride or rare earth metal or their alloys can be used as the second electrode, for example by having a metal fluoride layer formed on a metal.

The iridium or other metal complex can be mixed with a host material

The devices of the present invention can be used as displays in video displays, mobile telephones, portable computers and any other application where an electronically controlled visual image is used. The devices of the present invention can be used in both active and passive applications of such as displays.

In known electroluminescent devices either one or both electrodes can be formed of silicon and the electroluminescent material and intervening layers of a hole transporting and electron transporting materials can be formed as pixels on the silicon substrate. Preferably each pixel comprises at least one layer of an electroluminescent material and a (at least semi-) transparent electrode in contact with the organic layer on a side thereof remote from the substrate.

Preferably, the substrate is of crystalline silicon and the surface of the substrate may be polished or smoothed to produce a flat surface prior to the deposition of electrode, or electroluminescent compound. Alternatively a non-planarised silicon substrate can be coated with a layer of conducting polymer to provide a smooth, flat surface prior to deposition of further materials.

In one embodiment, each pixel comprises a metal electrode in contact with the substrate. Depending on the relative work functions of the metal and transparent electrodes, either may serve as the anode with the other constituting the cathode.

When the silicon substrate is the cathode an indium tin oxide coated glass can act as the anode and light is emitted through the anode. When the silicon substrate acts as the anode, the cathode can be formed of a transparent electrode which has a suitable work function; for example by an indium zinc oxide coated glass in which the indium zinc oxide has a low work function. The anode can have a transparent coating of a metal formed on it to give a suitable work function. These devices are sometimes referred to as top emitting devices or back emitting devices.

The metal electrode may consist of a plurality of metal layers; for example a higher work function metal such as aluminium deposited on the substrate and a lower work function metal such as calcium deposited on the higher work function metal. In another example, a further layer of conducting polymer lies on top of a stable metal such as aluminium.

Preferably, the electrode also acts as a mirror behind each pixel and is either deposited on, or sunk into, the planarised surface of the substrate. However, there may alternatively be a light absorbing black layer adjacent to the substrate.

In still another embodiment, selective regions of a bottom conducting polymer layer are made non-conducting by exposure to a suitable aqueous solution allowing formation of arrays of conducting pixel pads which serve as the bottom contacts of the pixel electrodes.

The invention claimed is:

1. An electroluminescent compound having the general chemical formula:

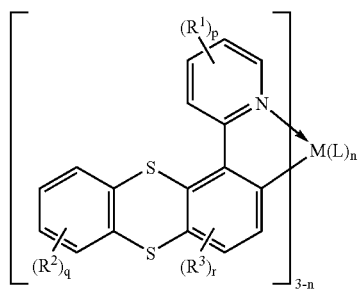

wherein:

L is selected from the group consisting of

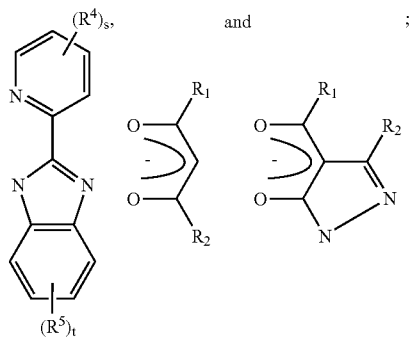

M is selected from the group consisting of ruthenium, rhodium, palladium, osmium, iridium and platinum;

n is 1 or 2;

$R_1$, $R_4$ and $R_5$ are the same or different and are independently selected from the group consisting of substituted and unsubstituted hydrocarbyl groups; substituted and unsubstituted monocyclic and polycyclic heterocyclic groups; substituted and unsubstituted hydrocarbyloxy and carboxy groups; fluorocarbyl groups; halogen; nitrile; amino; alkylamino; dialkylamino; arylamino; diarylamino; and thiophenyl;

p, s and t are independently selected from the integers 0, 1, 2 and 3, subject to the proviso that where any of p, s and t is 2 or 3 only one of the entities $R_1$, $R_4$ and $R_5$ can be other than saturated hydrocarbyl or halogen;

$R_2$ and $R_3$ are the same or different and are independently selected from the group consisting of substituted and unsubstituted hydrocarbyl groups and halogen; and, q and r are independently selected from the integers 0, 1 and 2.

2. The compound of claim 1, wherein M is iridium.

3. The compound of claim 1, wherein n is 1.

4. The compound of claim 1, wherein at least one of $R_1$, $R_4$ and $R_5$ is a substituted or unsubstituted aliphatic or cycloaliphatic group.

5. The compound of claim 4, wherein least one of $R_1$, $R_4$ and $R_5$ is alkyl or alkoxy.

6. The compound of claim 5, wherein at least one of $R_1$, $R_4$ and $R_5$ is selected from the group consisting of methyl, ethyl, n-propyl, i-propyl. s-butyl, t-butyl, cyclohexyl, methoxy and ethoxy.

7. The compound of claim 1, wherein at least one of $R_1$, $R_4$ and $R_5$ is a substituted or unsubstituted monocyclic or polycyclic aromatic, aryloxy or heterocyclic structure.

8. The compound of claim 7, wherein at least one of $R_1$, $R_4$ and $R_5$ is selected from the group consisting of phenyl, tolyl, fluorophenyl, biphenyl, naphthyl, fluorenyl, anthracenyl, phenanthrenyl and carbazolyl.

9. The compound of claim 1, wherein at least one of $R_1$, $R_4$ and $R_5$ is selected from the group consisting of fluoro, chloro, methylamino, dimethylamino, benzylamino and dibenzylamino.

10. The compound of claim 1, wherein at least one of $R_2$ and $R_3$ is a substituted or unsubstituted aliphatic group.

11. The compound of claim 10, wherein at least one of $R_2$ and $R_3$ is alkyl.

12. The compound of claim 11, wherein at least one of $R_2$ and $R_3$ is methyl or ethyl.

13. The compound of claim 1, wherein at least one of $R_2$ and $R_3$ is chloro or bromo.

14. The compound of claim 1, wherein M is Ir, n is 1 and p, q, r, s and t are each 0.

15. An electroluminescent device which comprises: (i) a first electrode; (ii) a second electrode; and (iii) a layer of an electroluminescent compound according to claim 1 located between said first and second electrodes.

16. The device of claim 15, wherein there is a layer of a hole transmitting material located between the first electrode and the layer of electroluminescent compound.

17. The device of claim 16, wherein the hole transmitting material is a polyaromatic amine.

18. The device of claim 15, wherein there is a layer of an electron transmitting material located between an electrode that functions as a cathode and the layer of electroluminescent compound.

19. The device of claim 18, wherein the electron transmitting material is either a metal quinolate or a material having the general chemical formula Ax(DBM)$_n$ where Ax is a metal, DBM is dibenzoyl methane, and n is the valence of Ax.

20. The device of claim 19, wherein the electron transmitting material is a metal quinolate selected from the group consisting of aluminum quinolate, zirconium quinolate and lithium quinolate.

* * * * *